United States Patent [19]

Sninsky et al.

[11] Patent Number: 5,389,512
[45] Date of Patent: Feb. 14, 1995

[54] METHOD FOR DETERMINING THE RELATIVE AMOUNT OF A VIRAL NUCLEIC ACID SEGMENT IN A SAMPLE BY THE POLYMERASE CHAIN REACTION

[75] Inventors: Shirley Y. Kwok, San Ramon; John J. Sninsky, El Sobrante, both of Calif.

[73] Assignee: Hoffman-La Roche Inc., Nutley, N.J.

[21] Appl. No.: 246,395

[22] Filed: May 20, 1994

Related U.S. Application Data

[63] Continuation of Ser. No. 669,923, Mar. 15, 1991, abandoned, which is a continuation of Ser. No. 254,889, Oct. 7, 1988, abandoned.

[51] Int. Cl.$^6$ .............................. C12Q 1/70; C12Q 1/68
[52] U.S. Cl. .......................................... 435/5; 435/6; 935/77; 935/78
[58] Field of Search ..................... 435/5, 6; 935/77, 78

[56] References Cited

U.S. PATENT DOCUMENTS

| | | | |
|---|---|---|---|
| 4,582,788 | 4/1986 | Erlich | 435/6 |
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,965,188 | 10/1990 | Mullis et al. | 435/6 |

FOREIGN PATENT DOCUMENTS

| | | | |
|---|---|---|---|
| 0229701 | 7/1987 | European Pat. Off. | 435/6 |
| 0237362 | 9/1987 | European Pat. Off. | 435/6 |
| 0258017 | 3/1988 | European Pat. Off. | 435/6 |
| 269445 | 6/1988 | European Pat. Off. | 435/6 |

OTHER PUBLICATIONS

Chelly et al., 1988, Nature 333:858–860.
Kashani-Sabet et al., 1988, Cancer Research 48:5775–5778.
Rappolee et al., 1988, Science 241:708–712.
Gilliland et al., 1989, J. Cell. Biochem. UCLA Symposia on Molecular and Cellular Biology, Abstract WH001.
Smith et al., 1989, J. Immuno. 118-265–272.
Wang et al., 1989, Proc. Natl. Acad. Sci. USA 86:9717.
Gilliland et al., "Competitive PCR for Quantitation of mRNA" PCR Protocols: A Guide to Methods and Applications ed. Innis et al., 1990, Academic Press, San Diego.
Kellog et al., 1990, Anal. Biochem. 189-202–208.
Kwok et al., 1987, J. Virology 61(5):1690–1694.
Weier et al., 1987, J. Soc. Analyt. Psychol. Cytology Abstract No. 113.
Duggan et al., 1988, Blood 71(4):1117–1123.
Ou et al., 1988, Science 239:295–297.
Lawrence Livermore Labs Invention Disclosure No. LL IL-7859 "Detection of Chromosomal Deletions".
Lawrence Livermore Labs Invention Disclosure No. LL IL-8093 "Determination of Gene Copy Number Using In Vitro DNA Amplification".
Kwok et al., 1988, Blood 72(4):1117–1123.
Alabaster et al., Canc. Res 38(4):1031–1035 (1978) abstr.
Brunk et al., Anal. Biochem. 92(2):497–500 (1979) abstr.
Raleigh et al., Anal. Biochem. 72(1-2):460–467 (1976) abstr.
Renfroe et al., J. Plant Physiol. 121(2):131–140 (1986). abstr.
Sander et al., Hum. Nutr. Clin. Nutr. 40(2):103–118 (1986). abstr.
Storb et al., J. Immunol. 117(1):259–268 (1976) abstr.
Toscani et al., Anal. Biochem. 165(2):309–319 (1987).

*Primary Examiner*—Stephanie W. Zitomer
*Attorney, Agent, or Firm*—George M. Gould; Dennis P. Tramaloni; Stacey R. Sias

[57] ABSTRACT

The present invention provides a method for determining the relative amount of a nucleic acid segment in a sample by the polymerase chain reaction. The method involves the simultaneous amplification of the nucleic acid segment and a second nucleic acid segment present in the sample. The amount of amplified DNA from each segment is determined and compared to standard curves to determine the amount of the nucleic acid segment present in the sample before amplification expressed as a ratio of first segment to second segment. The method is especially preferred for determining the viral load, or copies of virus genome/host cell, in a sample of cells from an individual infected with a virus.

14 Claims, No Drawings

METHOD FOR DETERMINING THE RELATIVE AMOUNT OF A VIRAL NUCLEIC ACID SEGMENT IN A SAMPLE BY THE POLYMERASE CHAIN REACTION

This application is a continuation, of application Ser. No. 07/669,923, filed Mar. 15, 1991, now abandoned, which is a continuation of application Ser. No. 07/254,889 filed Oct. 7, 1988, now abandoned.

BACKGROUND OF THE INVENTION

1. Field of the Invention

The present invention relates to the determination of the relative amount, and copy number, of a particular nucleic acid segment in a biological sample. The invention is particularly useful for determining the viral load, or the number of copies of a viral genome per cell, in a biological sample. The method is therefore especially applicable in the field of medical diagnostics but can also be applied in the fields of genetics, molecular biology, biochemistry, and forensics.

2. Description of Related Disclosures

U.S. Pat. Nos. 4,683,195 and 4,683,202 disclose methods for carrying out PCR, a nucleic acid amplification method, and for using PCR in the detection of specific nucleotide sequences PCR has been automated; the apparatus for automated PCR is disclosed in Ser. No. 899,061, filed Aug. 22, 1986, now abandoned, which is a continuation-in-part of Ser. No. 833,368, filed Feb. 25, 1986, now U.S. Pat. No. 5,331,586. The DNA polymerase of *Thermus aquaticus* (called Taq polymerase) is especially preferred for PCR; methods for purification and recombinant expression of Taq polymerase are disclosed in Ser. No. 143,441 filed Jan. 12, 1988, now abandoned, which is a continuation-in-part of copending Ser. No. 063,509, filed Jun. 17, 1987, which issued as U.S. Pat. No. 4,889,818, which is a continuation-in-part of copending Ser. No. 899,241, filed Aug. 22, 1986, now abandoned. Methods for structure-independent PCR using 7-deazaguanine are disclosed in copending Ser. No. 248,556, filed Sep. 23, 1988. Methods for inverse PCR are disclosed in copending Ser. No. 203,000, filed Jun. 6, 1988, now abandoned. PCR can be used to detect viral sequences in a sample, as disclosed in Ser. No. 934,955, filed Nov. 26, 1986, now abandoned, which is a continuation-in-part of copending Ser. No. 935,581, filed Nov. 26, 1986, now abandoned in favor of continuation application Ser. No. 394,276, which issued as U.S. Pat. No. 5,008,182. Ser. No. 935,581 is a continuation-in-part of copending Ser. No. 818,127, filed Jan. 10, 1986, now abandoned. Other viral detection methods utilizing PCR are disclosed in Ser. No. 935,271, filed Nov. 26, 1986, now abandoned, and copending Ser. No. 234,486, filed Sep. 9, 1988 now abandoned. DNA preparation solutions preferred for PCR are described in Ser. No. 178,202, filed Apr. 6, 1988, now abandoned. The disclosures of these related patents and publications are all incorporated herein by reference. European Patent Office Publication (EPO) No. 258,017 describes Taq polymerase, a preferred DNA polymerase for use in PCR. PCR has been used to detect the presence of vital nucleic acid sequences, as is disclosed in EPO Nos. 229,701 and 269,445. PCR is also especially useful for determining HLA type, as disclosed in EPO 237,362. Other HLA typing methods are disclosed in U.S. Pat. Nos. 4,582,788 and 4,683,194.

There is still a need in the art, however, for accurate and reliable methods for determining the amount and copy number of nucleic acid sequences in a sample, especially in relation to the copy number of another nucleic acid sequence in the sample. This determination can be of vital importance. For instance, the viral load of an individual, essentially a ratio of vital to individual genomic nucleic acid, can reveal whether a patient is responding to therapy. In the case of the viruses responsible for a disease such as AIDS, the importance of this determination cannot be overstated. The present invention provides a solution to this vital need.

SUMMARY OF THE INVENTION

The present invention provides a method for determining the relative amount of a nucleic acid segment in a sample that comprises: (a) amplifying by a polymerase chain reaction said nucleic acid segment and a second nucleic acid segment, wherein a pair of oligonucleotide primers specific for each segment are extended in the polymerase chain reaction by an agent for polymerization to yield the amplified segments; (b) measuring the amounts of amplified first and second segments produced in step (a); and (c) calculating from the amounts of amplified first and second segments produced in step (a), the amount of said first nucleic acid segment present in the sample before amplification.

DETAILED DESCRIPTION OF THE INVENTION

The present invention provides a method for determining the amount of a nucleic acid segment, relative to the amount of a second nucleic acid segment, in a sample. The method involves amplifying by a polymerase chain reaction two different segments of nucleic acid. The first segment is present in the sample in an unknown amount. A pair of oligonucleotide primers that are specific for each segment are extended in the polymerase chain reaction by an agent for polymerization to yield amplified segments that are specific for each segment. The amount of each amplified first and second segment produced in the polymerase chain reaction is measured, and from those amounts, the relative amount of the first segment present in the sample before amplification can be readily determined.

The relative amount of the first nucleic acid segment present in the sample before amplification is determined using two standard curves. The two standard curves are generated by, in the first, plotting the amount of the first segment produced in a polymerase chain reaction against varying, but known, amounts of first segment present before amplification. The second curve is generated by plotting the amount of the second segment produced in a polymerase chain reaction against varying, but known, amounts of second segment present before amplification.

The amount of the first nucleic acid segment produced in the polymerase chain reaction is first compared to the standard curve for the first segment to determine an amount of first segment present in the sample before amplification. The amount of the second segment produced in the polymerase chain reaction is then compared to the standard curve for the second segment to determine the amount of second segment present in the sample before amplification. The amount of the first segment present in the sample before amplification is then expressed as a ratio of first to second segment, such as viral segments to cellular DNA segments.

The method of the invention is far more accurate than when the amount of a nucleic acid segment in a sample is determined by comparison to a single standard curve. The method is especially useful in that the second segment amplified in the method need not be present in the sample in a known amount.

The present invention is illustrated below by determination of the viral load in a biological sample. Viral load can reveal the seriousness of a disease and the effectiveness of therapy. The virus present in the sample is human immunodeficiency virus (HIV), also known as the AIDS virus. The viral load is expressed as copies of viral genome per cell (or per cell genome) present in the sample.

Thus, in this illustrative embodiment of the invention, the first nucleic acid segment is a segment of the genome of the AIDS virus; the primers used to amplify the AIDS segment of nucleic acid in this embodiment amplify either a 115 bp or 130 bp segment of the gag gene. The AIDS viruses, including HIV-I and HIV-II, are RNA viruses but can exist in double-stranded DNA form. PCR can be used to amplify RNA, but reverse transcriptase is utilized to first form a cDNA copy of the RNA. The cDNA segment is then amplified by PCR. The second nucleic acid segment in this illustrative embodiment is the human HLA DQα gene, present in human cells at two copies per cell. The primers used to amplify HLA DQα in this embodiment amplify a 242 bp segment of the HLA DQα gene.

The standard curves for use in this embodiment of the invention involve a series of reactions carried out on a variety of samples containing different but known amounts of human placental DNA (human placental DNA can be obtained from Sigma Chemical Company). The primer concentration and other reaction components and conditions are kept constant in each reaction. The amount of amplified DNA is measured, and a standard curve (initial amount of genomic DNA versus amount of amplified DNA produced) is generated. The initial amount of genomic DNA present can be expressed in grams or by copy number, because one cell contains one genome copy, and a human genome is about 7 picograms (pg). As used herein, "human genome" refers to the diploid genome of a human cell.

In a similar fashion, a standard curve for the nucleic acid segment of the AIDS virus is generated. In the illustrative embodiment of the invention, the standard curve for the AIDS virus genome is generated utilizing known amounts of plasmid 495, which contains a complete copy of the HIV-I genome and was obtained from the Center for Disease Control.

The standard curves are generated and used to determine the amount of, in the illustrative embodiment of the invention, AIDS virus genomes per cell (or per human genome) present in a given sample. The present invention requires that the amplification of the first and second segments of nucleic acid be carded out in the same reaction. Those skilled in the an will recognize from the foregoing that one could determine viral load by performing the genomic DNA and viral nucleic acid amplifications in separate reactions. However, he accuracy of such a method is dependent on the degree to which the cell lysis and amplification steps proceed with similar efficiency for both amplifications. By performing both amplifications in the same reaction, one ensures excellent accuracy.

This simultaneous amplification of two different nucleic acid segments cannot, however, be efficiently carried out simply by adding equal amounts of the four PCR primers (two primers in each pair; one pair for each segment) to the PCR reaction when one of the segments is present at a much lower level than the other segment. This is typically the case when a segment of the AIDS virus is the first nucleic acid segment, and the second nucleic acid segment is from a gene present at two copies per cell (such as the DQα gene). Samples from AIDS patients, for example, usually contain one copy of the AIDS virus (either HIV-I or HIV-II) genome per every 100 to 10,000 cells. If the two primer pairs used in the method of the invention are present in equimolar amounts, the amplification of the segment present at two copies per genome proceeds far more efficiently than the amplification of the AIDS virus nucleic acid segment and can mask the signal from the AIDS segment. This problem is readily overcome, however, by adjusting the relative amounts of the two pairs of primers used in the amplification so that the concentration of the primer pair for amplification of the segment present in the greatest amount is much lower than that of the other primer pair.

Thus, preferred conditions for the method of the present invention when used to determine the viral load of an AIDS patient include utilization of samples that contain about one to three $\mu$g of genomic DNA (1 $\mu$g of human genomic DNA represents about 150,000 cells). About 50 picomoles of the primers specific for the AIDS virus segment are present in the reaction, but only from 300 femtomoles to 2 picomoles of the primers specific for the human genomic segment are present in the reaction.

Although variant amounts of primers can be used to achieve efficient amplification of both segments when one segment in the sample is present in much larger amounts than the other segment, other techniques can also be employed for purposes of the present invention. For instance, the primers specific for the segment present in abundance in the sample could be shorter than the primers specific for the segment present in much lower quantities. Alternatively, the primers specific for the abundant segment can be designed to amplify a segment (i.e., 500 bp) much larger than the segment amplified by the primers specific for the segment present in much lower quantities. In this embodiment, the 62 kilodalton variant of Taq polymerase is preferred, because the 62 kilodalton variant is relatively inefficient at extending beyond about 250 bp. Taq polymerase, unlike Other DNA polymerases, is active at high temperatures.

The method of the invention is broadly applicable but is especially preferred for the detection of infectious agents present in biological samples. If the biological samples are samples of human cells, the utilization of a primer pair specific for an HLA gene segment, such as an HLA DQα gene segment, is preferred. The amplified HLA DNA can also be utilized to keep track of samples. As is well known in the art, the HLA loci provide a genetic fingerprint of an individual. Thus, amplified HLA DNA can be utilized to identify the individual from whom the sample was taken. In addition, the HLA loci contain sequences indicative of disease susceptibility, and these sequences can be detected in conjunction with the present method.

The amount of amplified DNA generated in the method of the present invention can be measured in many different ways. For instance, labeled primers or nucleotides can be utilized in PCR, and the incorporation of label can be measured to determine the amount of amplified DNA. The label can be isotopic or non-isotopic. Alternatively, the amount of amplified product can be determined by electrophoresis and visualization of amplified product by staining or by hybridization with a labeled probe. When a labeled probe is utilized, the probe should be present in excess of amplified product. In one such embodiment of the invention, the amplified product is denatured, hybridized to labeled probes, and the resulting mixture is electrophoresed on an agarose or acrylamide gel. The amount of probe on the gel in the areas where the products are expected to migrate is then measured.

The method of the invention requires that the amplified amounts of a first and second segment produced in a single polymerase chain reaction be determined. Thus, the method requires that the amplified first segment be distinguishable from the amplified second segment. If the segments are of different sizes, then it is relatively simple to distinguish one amplified segment from the other, i.e., the amplified products can be readily separated by gel electrophoresis. The present invention does not require that the amplified product be of different sizes, however, for other methods can be utilized to distinguish one amplified segment from another. For instance, the primers (or probes) specific for one segment can be labeled differently than the primers (or probes) specific for the other segment.

The method of the invention is exemplified below, but those skilled in the art recognize the present invention is broadly applicable and in no way limited to the specific embodiments described below.

EXAMPLE 1

Polymerase Chain Reaction

A. Primers and Probes

Primers SK38 and SK39 amplify an approximately 115 bp segment of the HIV-I gag gene.

```
SK38  5' AT AAT CCA CCT ATC CCA GTA GGA GAA AT
SK39  5' TTT GGT CCT TGT CTT ATG TCC AGA ATG C
```

Primers SK101 and SK145 amplify an approximately 130 bp segment of either the HIV-I or HIV-II gag gene. Primers SK101 and SK145 are not exactly complementary to the HIV gag gene but an exactly complementary primer could also be utilized.

```
SK101  5' GCT ATG TCA GTT CCC CTT GGT TCT C
SK145  5' AGT GGG GGG ACA TCA AGC AGC CAT GCA AAT
```

Primers GH26 and GH27 amplify an approximately 242 bp segment of the HLA DQα gene. These primers also contain some non-complementary sequences.

```
GH26  5' GT GCT GCA GGT GTA AAC TTG TAC CAG
GH27  5' CAC GGA TCC GGT AGC AGC GGT AGA GTT G
```

Probe SK19 is for use with primers SK38 and SK39.

```
SK19  5'ATCCTGGGATTAAATAAAATAGTAAGAATGTATAGCCCTAC
```

Probe SK102 is for use with primers SK101 and SK145.

```
SK102  5' GAGACCATCAATGAGGAAGCTGCAGAATGGGAT
```

Probes SK264 and GH64 are for use with primers GH26 and GH27.

```
GH64   5' TGGACCTGGAGAGGAAGGAGACTG
SK264  5' AGTTCTACGTGGACCTGGACAGGAAGGAGACTGC
```

B. Procedure for Isolating DNA From Peripheral Blood Mononuclear Cells PBMCs)

About 10 ml of blood are collected from the patient. The mononuclear cells are purified from 4 ml of blood by centrifugation in a Ficoll-paque ® (from Pharmacia) gradient. The PBMC band is collected into a 15 ml polystyrene tube. The PBMCs are washed with at least 3 ml of Hank's balanced salt solution or phosphate buffered saline solution (PBS). The PBMCs are collected by centrifugation, and the wash step is repeated twice. The PBMC pellet is resuspended in 200 µl of Solution A. Solution A is 100 mM KCl; 10 mM Tris-HCl, pH 8.3; and 2.5 mM $MgCl_2$. The mixture is transferred to a Sarstedt tube containing an equal volume (typically 200 µl) of Solution B. Solution B is 10 mM Tris-HCl, pH 8.3; 2.5 mM $MgCl_2$; 1% Tween 20; and 1% NP40. Proteinase K is then added to the mixture to achieve a final concentration of 120 µg/ml. Proteinase K (5 mg/ml) should be self-digested and stored frozen. After the addition of proteinase K, the mixture is incubated at 60° C. for 1 hour. After the incubation, the proteinase K is inactivated by incubation at 95° C. for 10 minutes. The samples are then ready for PCR amplification.

C. Thermocycling Profile

Reactions were carried out on a Perkin-Elmer/Cetus Instruments Thermal Cycler for 30 cycles. In each cycle, the reactions were heated to 94° C. for one second, incubated at 94° C. for 25 seconds, cooled to 55° C. for one second, incubated at 55° C. for 30 seconds, heated to 72° C. for one second, and incubated at 72° C. for 60 seconds. The one second intervals described alive are ramp intervals; the actual sample will take longer to reach the indicated temperature.

D. Reaction Mixtures

Ten µl of 10X Taq buffer are mixed with 1 µl each of primer pairs SK38/SK39 or SK101/SK145 at a concentration of 50 picomoles of each primer of the pair per µl. One µl of GH26 (1 picomole), 1 µl of GH27 (1 picomole), 2 µl of a solution 40 mM in each of the deoxyribonucleotide triphosphates, 2.5 units of Taq polymerase (Perkin-Elmer/Cetus Instruments), and the sample DNA are also added, and the reaction volume is brought to 100 µl with $H_2O$. 10X Taq buffer is 500 mM KCl; 25 mM $MgCl_2$; 100 mM Tris-HCl, pH 8.3; and 0.1% weight/volume gelatin.

EXAMPLE 2

Detection of Amplified Product by Oligomer Hybridization

Thirty μl of the amplification reaction are added to 10 μl of probe mix containing 66 mM NaCl, 44 mM EDTA (pH 8.0), and 0.25 picomoles of each probe, either SK19 or SK102 and either GH64 or SK264 at a specific activity of 3 to 5 μCi/picomole. The samples are overlaid with oil and incubated at 95° C. for 5 minutes and immediately placed in a 55° C. water bath. The probes are allowed to anneal at 55° C. for at least 15 minutes.

Bromophenol blue is added to the sample, and the oil is extracted with chloroform. The sample is electrophoresed on a 10% polyacrylamide gel until the bromophenol blue reaches the gel front. The gel is blotted dry, wrapped in plastic, and allowed to expose Kodak XAR®5 film with a single intensifying screen for about 16 hours at −70° C. The signal on the autoradiogram is measured and compared with standard curves to determine the copies of AIDS virus per human genome in the sample. The signal is measured using an Ambis scanning device according to the manufacturer's protocol.

Other modifications of the embodiments of the invention described above that are obvious to those of ordinary skill in the areas of molecular biology, medical diagnostic technology, biochemistry, virology, genetics, and related disciplines are intended to be within the scope of the accompanying claims.

We claim:

1. A method for determining the amount of a viral nucleic acid sequence relative to the amount of a cellular nucleic acid sequence in a sample comprising virally infected host cells, comprising the steps of:
   (a) co-amplifying the viral nucleic acid sequence and the cellular nucleic acid sequence in an amplification reaction mixture that comprises a first primer pair for amplifying said viral nucleic acid sequence, a second primer pair for amplifying said cellular nucleic acid sequence and DNA polymerase, wherein the relative concentrations of said first and second primer pairs are adjusted so that the concentration of the primer pair for amplification of the nucleic acid sequence present in the greatest amount is lower than the concentration of the primer pair for amplification of the nucleic acid sequence present in the smallest amount,
   (b) measuring the amounts of amplified viral and cellular nucleic acid sequences produced in step (a); and
   (c) determining the amount of said viral nucleic acid sequence relative to the amount of said cellular nucleic acid sequence present in said sample prior to the co-amplification in step (a).

2. The method of claim 1, wherein said DNA polymerase is Taq polymerase.

3. The method of claim 1, wherein said first primer pair is present in said amplification reaction mixture at a concentration higher than that of said second primer pair.

4. The method of claim 3, wherein said viral nucleic acid sequence is indicative of a disease state.

5. The method of claim 4, wherein said genomic sequence is a segment of human cellular nucleic acid DNA.

6. The method of claim 5, wherein said amplified viral and cellular nucleic acid sequences are distinguishable by size.

7. The method of claim 5, wherein said genomic DNA is from an HLA locus.

8. The method of claim 1, wherein said sample comprises viral nucleic acid in the range of 1 copy per every 100 to 10,000 cells.

9. The method of claim 1, wherein said viral nucleic acid is a segment from an AIDS virus.

10. The method of claim 7, wherein said second primer pair is GH26/GH27.

11. The method of claim 9, wherein said first primer pair is SK38/SK39.

12. The method of claim 9, wherein said first primer pair is SK101/SK145.

13. The method of claim 1, wherein the amplification reaction mixture comprises about 50 picomoles of the first primer pair, about 300 femtomoles to about 2 picomoles of the second primer pair, and the cellular nucleic acid sequence is about 1 to 3 μg of cellular DNA.

14. The method of claim 3 wherein the concentration of the first primer pair is related to the concentration of the second primer pair by a ratio in a range of from about 170-fold higher concentration to about a 25-fold higher concentration.

* * * * *

UNITED STATES PATENT AND TRADEMARK OFFICE
CERTIFICATE OF CORRECTION

PATENT NO. : 5,389,512

DATED : February 14, 1995

INVENTOR(S) : Shirley Y. Kwok and John J. Sninsky

It is certified that error appears in the above-identified patent and that said Letters Patent is hereby corrected as shown below:

In column 8, Claim 5, line 1, please delete "genomic" and insert --cellular nucleic acid--.

In column 8, Claim 5, line 2, please delete --cellular nucleic acid--.

Signed and Sealed this

Twentieth Day of June, 1995

BRUCE LEHMAN

*Attest:*

*Attesting Officer*       *Commissioner of Patents and Trademarks*